United States Patent [19]

Ferres et al.

[11] 4,166,817

[45] Sep. 4, 1979

[54] PENICILLINS

[75] Inventors: Harry Ferres, Epsom; Frank P. Harrington, Tilgate, both of England

[73] Assignee: Beecham Group Limited, United Kingdom

[21] Appl. No.: 886,033

[22] Filed: Mar. 13, 1978

[30] Foreign Application Priority Data

Mar. 16, 1977 [GB] United Kingdom ............... 11234/77

[51] Int. Cl.² ............................................ C07D 499/68
[52] U.S. Cl. ................................. 260/239.1; 424/271
[58] Field of Search ..................... 260/239.1; 424/271, 424/246

[56] References Cited

U.S. PATENT DOCUMENTS

| | | | |
|---|---|---|---|
| 3,268,513 | 8/1966 | Grant et al. | 260/239.1 |
| 3,340,252 | 9/1967 | Alburn et al. | 260/239.1 |
| 3,433,784 | 3/1969 | Long et al. | 260/239.1 |
| 3,953,428 | 4/1976 | Murakami et al. | 260/239.1 |
| 4,008,220 | 2/1977 | Tobiki et al. | 260/239.1 |

*Primary Examiner*—Gerald A. Schwartz
*Attorney, Agent, or Firm*—Jacobs & Jacobs

[57] ABSTRACT

New penicillin antibiotics are disclosed which are effective antibacterial agents and which belong to the class of α-(heterocyclic acylamino) penicillins and their salts and esters together with pharmaceutical compositions containing the same and their method of administration. The new compounds are characterized by having an amino substituent on the heterocyclic ring which is linked through an acylamino group to the α-carbon atom of the penicillin side chain. Procedure for preparing the new penicillins is described as well as the antibacterial activity of exemplary compounds against typical microorganisms.

21 Claims, No Drawings

PENICILLINS

This invention relates to penicillin antibiotics and in particular to a class of α-(heterocyclic acylamino) penicillins which are of value as antibacterial agents.

Our British Pat. No. 1,130,445 discloses and claims α-(heterocyclic acylamino) penicillins of formula (A):

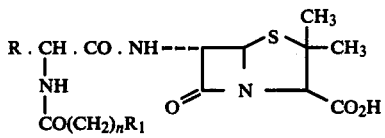

and non-toxic salts thereof, where R is a phenyl or thienyl group, $R_1$ is a heterocyclic group which may be substituted and n is zero or 1.

Within this class of penicillins, several sub-groups of penicillins have been described, for example those in British Pat. Nos. 1,407,566 and 1,409,177 and U.S. Pat. No. 3,864,329, which are characterised by having an oxygen function (such as a ketone, or an optionally etherified or esterified hydroxy group) on the heterocyclic ring.

It has now been found that α-(heterocyclic acylamino) penicillins having an amino substituent on the heterocyclic ring exhibit broad spectrum antibacterial activity and in particular are active against Pseudomonas organisms.

The present invention provides a penicillin of formula (I) or a pharmaceutically acceptable non-toxic salt or in vivo hydrolysable ester thereof:

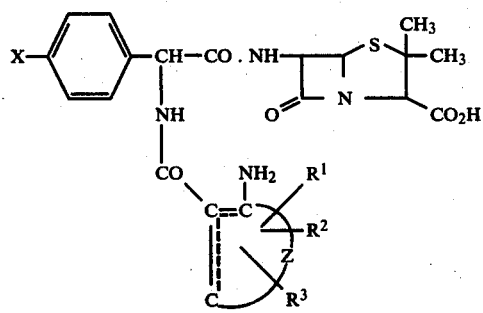

wherein
X is hydrogen or hydroxy;
the dotted line represents a double bond in one of the positions shown;
Z represents the residue of a 6-membered heterocyclic ring containing one or two nitrogen atoms;
$R^1$, $R^2$ and $R^3$ are the same or different and each represents hydrogen, halogen, $C_{1-6}$alkyl, $C_{1-6}$alkoxy, $C_{1-6}$alkylthio, cyano, amino, mercapto, $C_{1-6}$alkylamino, di-$C_{1-6}$alkylamino, $C_{1-6}$alkanoylamino, nitro or hydroxy or any two of $R^1$, $R^2$ and $R^3$ on adjacent carbon or nitrogen atoms represent the residue of a fused 5- or 6-membered carbocyclic or heterocyclic ring containing up to three heteroatoms selected from oxygen, sulphur and nitrogen, and being optionally substituted with up to three substituents selected from halogen, $C_{1-6}$alkyl, $C_{1-6}$alkoxy, $C_{1-6}$alkylthio or hydroxy.

The compounds of the present invention include the pharmaceutically acceptable non-toxic esters of compound (I). Suitable esters include those which hydrolyse readily in the human body to produce the parent acid, for example alkoxyalkyl esters such as methoxymethyl esters, acyloxyalkyl esters such as acetoxymethyl, pivaloyloxymethyl, α-acetoxyethyl, α-acetoxybenzyl and α-pivaloyloxyethyl esters; alkoxycarbonyloxyalkyl esters, such as ethoxycarbonyloxymethyl and α-ethoxycarbonyloxyethyl; and lactone, thiolactone and dithiolactone esters, i.e. ester groups of formula (II):

wherein X' and Y' are oxygen or sulphur and Z' is an ethylene group or a 1,2-phenylene group optionally substituted by lower-alkoxy, halogen or nitro.

Preferred ester groups are the phthalidyl and 3,4-dimethoxy phthalidyl esters.

Suitable salts of the compound of formula (I) include metal salts, e.g. aluminium, alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxyethyl)-amine, tris(hydroxymethyl)amine or tris-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline, or other amines which have been used to form salts with penicillins.

Pharmaceutically acceptable acid addition salts of such a compound are also included within this invention. Suitable acid addition salts of the compounds of formula (I) include, for example inorganic salts such as the sulphate, nitrate, phosphate, and borate; hydrohalides e.g. hydrochloride, hydrobromide and hydroiodide; and organic acid addition salts such as acetate, oxalate, tartrate, maleate, citrate, succinate, benzoate, ascorbate, methanesulphonate and p- toluenesulphonate, trifluoroacetate.

Suitable examples of the substituents $R^1$, $R^2$ and $R^3$ include chloro, bromo, fluoro, methyl, ethyl, n- and iso-propyl, n-, sec-iso- and tert-butyl, methoxy, ethoxy, n- and iso-propoxy, n-, sec-iso- and tert-butoxy, methylthio, ethylthio, n- and iso-propylthio, cyano, amino, mercapto, nitro, methylamino, ethylamino, dimethylamino, diethylamino, acetylamino, formyl.

The moiety Z may complete a pyridine, pyrimidine, pyridazine, or 1,2,3-triazine ring.

When two of the groups $R^1$, $R^2$ and $R^3$ complete a further fused, saturated or unsaturated carboxylic or heterocyclic ring, examples of such rings include benzene, cyclohexane, cyclopentane, pyridine, pyrimidine, pyridazine, pyrazine, piperidine, piperazine, pyrrolidine, pyrazole, triazole, tetrazole, oxazole, triazine, thiazoline, thiazolidine, morpholine.

Such a fused ring may be attached to either a carbon or a nitrogen atom in the moiety Z.

Examples of specific compounds of the present invention include:
6-[D-α-(4-aminoquinolin-3-carboxamido)-phenylacetamido]penicillanic acid;

6-[D-α-(4-aminoquinolin-3-carboxamido)-4-hydroxyphenylacetamido]penicillanic acid;
6-[D-α-(7-aminopyrazolo[1,5-a]pyrimidine-6-carboxamido]phenylacetamido penicillanic acid;
6-[D-α-(7-aminopyrazolo[1,5-a]pyrimidine-6-carboxamido]-4-hydroxyphenylacetamido penicillanic acid;
6-[D-α-(2-aminopyridine-3-carboxamido)-phenylacetamido]penicillanic acid;
6-[D-α-(2-aminopyridine-3-carboxamido)4-hydroxyphenylacetamido]penicillanic acid;
6-[D-α-(5-amino-1,8-naphthridine-6-carboxamido)-phenylacetamido]penicillanic acid;
6-[D-α-(5-amino-1,8-naphthridine-6-carboxamido)-4-hydroxyphenylacetamido]penicillanic acid;
6-[D-α-(4-amino-1,5-naphthridine-3-carboxamido)-phenylacetamido]penicillanic acid;
6-[D-α-(4-amino-1,5-naphthridine-3-carboxamido)-4-hydroxyphenylacetamido]penicillanic acid;
6-[D-α-(2-aminopyridazine-3-carboxamido)-phenylacetamido]penicillanic acid;
6-[D-α-(2-aminopyridazine-3-carboxamido)-4-hydroxyphenylacetamido]penicillanic acid.
6-[D-α-(4-amino-7-methyl-1,8-naphthridine-3-carboxamido)phenylacetamido]penicillanic acid;
6-[D-α-(4-amino-7-methyl-1,8-naphthridine-3-carboxamido)-4-hydroxyphenylacetamido]penicillanic acid;
6-[D-α-(4-amino-7-chloroquinoline-3-carboxamido)-phenylacetamido]penicillanic acid;
6-[D-α-(4-amino-7-chloroquinoline-3-carboxamido)-4-hydroxyphenylacetamido]penicillanic acid.

The compounds of formula (I) may be prepared by reacting a compound of formula (III) or an N-protected derivative thereof:

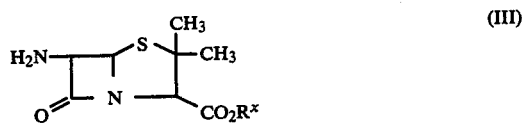

(III)

wherein $R^x$ is hydrogen, an in vivo hydrolysable ester radical or a carboxyl blocking group; with an N-acylating derivative of an acid of formula (IV):

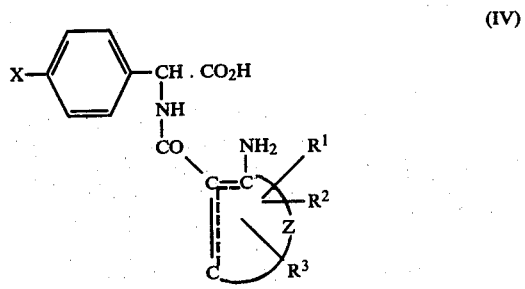

(IV)

wherein $X, Z, R^1, R^2$ and $R^3$ as defined with respect to formula (I) above and wherein any amino and hydroxy groups may be blocked; and thereafter if necessary carrying out one or more of the following steps:
(i) removal of any N-protecting groups by hydrolysis or alcoholysis;
(ii) removal of any carboxyl blocking groups;
(iii) removal of any amino or hydroxy blocking groups;
(iv) converting the product to a salt or ester thereof.

Examples of "N-protected derivatives" of compound (III) include S-silyl and N-phosphorylated derivatives.

By the term "N-silyl derivative" of compound (III), we mean the product of reaction of the 6-amino group of compound (III) with a silylating agent such as a halosilane or a silazane.

Preferred silylating agents are silyl chlorides, particularly trimethylchlorosilane, and dimethyldichlorosilane.

The term "N-phosphorylated" derivative of compound (III) is intended to include compounds wherein the 6-amino group of formula (III) is substituted with a group of formula:

—P.$R_a R_b$ wherein $R_a$ is an alkyl, haloalkyl, aryl, aralkyl, alkoxy, haloalkoxy, aryloxy, aralkloxy or dialkylamino group, $R_b$ is the same as $R_a$ or is halogen or $R_a$ and $R_b$ together form a ring.

Suitable carboxyl-blocking derivatives for the group —$CO_2R^x$ in formula (III) include salts and ester derivatives of the carboxylic acid. The derivative is preferably one which may readily be cleaved at a later stage of the reaction. Suitable salts include tertiary amine salts, such as those with tri-loweralkylamines, N-ethylpiperidine, 2,6-lutidine, pyridine, N-methylpyrrolidine, dimethylpiperazine. A preferred salt is with triethylamine.

The carboxyl group may be regenerated from any of the above esters by usual methods appropriate to the particular $R^x$ group, for example, acid- and base-catalysed hydrolysis, or by enzymically-catalysed hydrolysis.

A reactive N-acylating derivative of the acid (IV) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a ($C_{2-6}$)-1,2-alkylene oxide—such as ethylene oxide or propylene oxide. The acylation reaction using an acid halide may be carried out at a temperature in the range −50° to +50° C., preferably −20° to +30° C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester of ketone, such as methyl isobutyl ketone or butyl acetate.

The acid halide may be prepared by reacting the acid (IV) or a salt thereof with a halogenating (e.g. chlorinating or brominating) agent such as phosphorus pentachloride, thionyl chloride or oxalyl chloride.

Alternatively, the N-acylating derivative of the acid (IV) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst. Another type of anhydride is the 2,5-oxazolidinedione of formula (V):

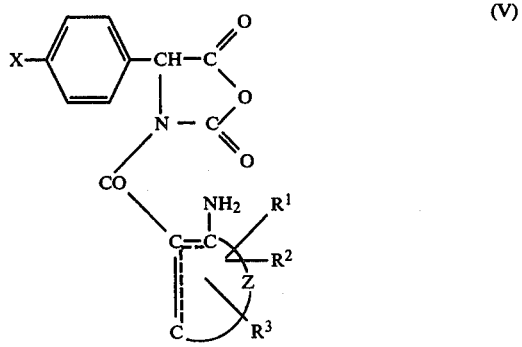

wherein X,Z,R$^1$, R$^2$ and R$^3$ are as defined with respect to formula (I) above. Compound (V) may be prepared from the acid (IV) by the action of phosgene.

Alternative N-acylating derivatives of acid (IV) are the acid azide, or activated esters such as esters with 2-mercaptopyridine, cyanomethanol, p-nitrophenol, 2,4-dinitrophenol, thiophenol, halophenol, including pentachlorophenol, monomethoxyphenol or 8-hydroxyquinoline; or amides such as N-acylsaccharins or N-acylphthalimides; or an alkylidene iminoester prepared by reaction of the acid (IV) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (IV) include the reactive intermediate formed by reaction in situ with a condensing agent such as a carbodiimide, for example, N,N-diethyl-, dipropyl- or diisopropylcarbodiimide, N,N'-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; and isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

In the above process, when any of the groups X, R$^1$, R$^2$ and R$^3$ represent a hydroxy group, it may be protected prior to the acylation reaction by known methods, for example by esterification or acylation. In general however, hydroxyl protection is not required.

The amino substituent on the heterocyclic ring in formula (IV) may also be blocked. By a blocked amino group is meant an amino group substituted with a group which can be removed after the acylation reaction under conditions sufficiently mild to avoid destruction of the molecule; or a group which can be converted to an amino group, again under mild conditions.

Examples of blocked amino groups include the protenated amino group (NH$_3^+$) which after the acylation reaction can be converted to the free amino group by simple neutralisation; and the β,β,β-trichloroethoxycarbonylamino radical which may be converted to amino by reduction with zinc in acetic acid.

Blocked amino groups which regenerate the amino group by catalytic hydrogenation include benzyloxycarbonylamino; p-substituted benzyloxycarbonylamino where the substituent is halogen (especially chlorine), nitro, or methoxy; triphenylmethyl; azido or nitro. The hydrogenation is preferably carried out at room temeprature and either at atmospheric or slightly elevated pressure. Preferred catalysts are noble metal catalysts for instance palladium or platinum, or Raney-nickel. Reduction of these groups may also be effected by electrolytic reduction.

Groups which regenerate the amino group on mild acid hydrolysis include the tert-butyloxycarbonylamino group which may be converted to amino by treatment with trifluoroacetic acid, hydrogen chloride, or p-toluenesulphonic acid.

Another example of a blocked amino group which may be subsequently converted to amino by mild acid hydrolysis is a group of formula:

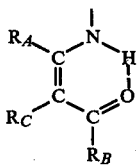

wherein R$_A$ is an alkyl, aralkyl, or aryl group, R$_B$ is an alkyl, aralkyl, aryl, alkoxy, aralkoxy or aryloxy group, and R$_C$ is a hydrogen atom or an alkyl, aralkyl, or aryl group, or R$_C$ together with either R$_A$ or R$_B$ completes a carbocyclic ring.

Other blocked amino groups include bromine which may be converted by amination, for instance with hexamethylenetetramine; o-nitrophenylsulphenylamino which may be converted to amino by reaction with sodium or potassium iodide sodium thiosulphate, sodium hydrosulphide, sodium hydrosulphite, or potassium thiocyanate.

The compounds of formula (I) may also be prepared by reaction of a compound of formula (XI) or an N-protected derivative thereof:

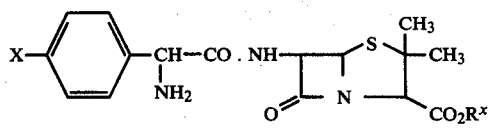

wherein X is as defined with respect to formula (I) and R$^x$ is a carboxyl blocking group; with an N-acylating derivative of an acid of formula (IX):

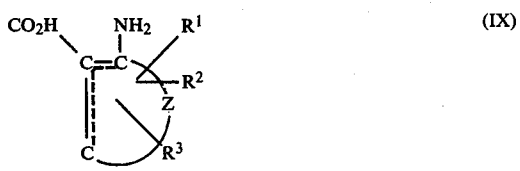

(IX)

wherein Z, $R^1$, $R^2$, and $R^3$ are as defined with respect to formula (I) above and wherein the amino and any hydroxy groups may be blocked; and thereafter if necessary carrying out one or more of the following steps:

(i) removal of any N-protecting groups by hydrolysis or alcoholysis;
(ii) removal of any carboxyl blocking groups;
(iii) removal of any amino or hydroxy blocking groups;
(iv) converting the product to a salt or ester thereof.

The comments made earlier concerning N-protected derivatives blocking groups and N-acylating derivatives also apply to this process.

In particular a preferred blocked amino group is the azide group. Alternatively an N-acylating derivative of an acid (IX) may also be employed with the free amino group.

A preferred N-acylating derivative of the acid (IX) is the anhydride (X):

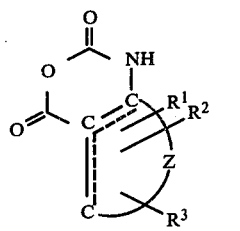

wherein $Z, R^1$, $R^2$ and $R^3$ are as defined with respect to formula (I).

The antibiotic compounds according to the invention may be formulated for administration in any convenient way for use in human and veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50–500 mg., of the active ingredient. The dosage as employed for adult human treatment will preferably range from 100 to 3000 mg., per day, for instance 1500 mg., per day, depending on the route and frequency of administration.

The compound of formula (I) may be the sole therapeutic agent in the compositions of the invention or a combination with other antibiotics may be employed. Advantageously the compositions also comprise a compound of formula (XIII) or a pharmaceutically acceptable salt or ester thereof:

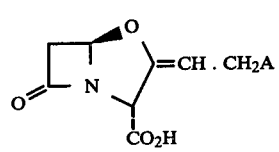

wherein A is hydrogen or hydroxyl.

Preferably the compound of formula (XIII) is clavulanic acid of formula (XIV) or a pharmaceutically acceptable salt or ester thereof:

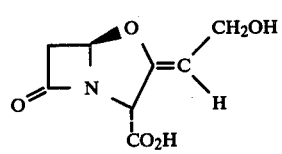

The preparation of these compounds is described in Belgium Pat. Nos. 827,926, 836,652 and West German Offenlegungsschrift No. 2,616,088.

It will be clear that the side-chain of the penicillins of formula (I) contains a potentially asymmetric carbon atom. This invention includes all the possible epimers of compounds (I) as well as mixtures of them.

The following examples illustrate the preparation of some of the compounds of this invention.

The following literature references are referred to in the Examples:

1. B. Riegel, et al. J. Amer Chem. Soc. 1946, 68, 1265.
2. Makisami, et al., Chem. Pharm. Bull, 10(7), 620-6 (1962).
3. A. L. J. Beckwith and R. J. Hickman, J. Chem. Soc. (C) 2756 (1968).

EXAMPLE 1

(a) 4-Azido-3-carbethoxyquinoline

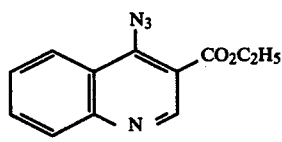

3-Carbethoxy-4-chloroquinoline[1](1.8 g; 0.0076 M) was dissolved in dry DMF (15 ml) at ambient temperatures and sodium azide (0.8 g; 0.012 M) added. The mixture was stirred at ambient tempertures for 24 hr. A large volume of Et$_2$O (250 ml) was added followed by H$_2$O (25 ml) and the layers separated. The aqueous phase was further extracted with Et$_2$O (2×25 ml), the Et$_2$O extracts combined, washed well with saturated brine, dried over anhydrous MgSO$_4$, filtered and the solvent removed in vacuo to yield a white solid, 1.77 g. (96%), m.p. 52°-53° C., (Found: C; 59.67; H, 4.13; N, 23.22% C$_{12}$H$_{10}$N$_4$O$_2$ requires C, 59.50; H, 4.13; N, 23.14%) $\nu_{max}$ (KBr) 2130, 1712, 1583, 1494, 1390, 1378, 1322, 1240, 857 cm$^{-1}$ δ[(CD$_3$)$_2$SO] 1.4(t), 4.49(q) (CH$_3$CH$_2$), 7.56-8.5(m) 9.15(s) (aromatic protons), m/e 242(M+).

(b) 4-Azido-3-quinolinic acid

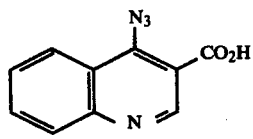

4-Azido-3-carbethoxyquinoline (1.4 g; 0.006 M) was suspended in 10% aq. NaOH at ambient temperatures and the mixture stirred until complete solution had been obtained. The solution was filtered, cooled to 0° C. and acidified to pH 4 with 5 M HCl. The resulting precipitate was filtered, washed well with H$_2$O and dried in vacuo over P$_2$O$_5$ to yield the product, 1.3 g (93%), as a monohydrate, m.p. 284° C. (dec.) (Found: N, 24.53%, C$_{10}$H$_8$N$_4$O$_3$ requires: N, 24.46%), $\nu_{max}$ (nujol) 3200-3700(br), 2200-2600(br), 2110, 1700, 1492, 1327, 1215, 760cm$^{-1}$, δ[(CD$_3$)$_2$SO] 7.45-3.1(m), 8.9(s) (aromatic protons). 14-16 (broad) (CO$_2$H*+H$_2$O), Exchangeable with D$_2$O.

(c) N-[4-Azido-3-quinolinoyloxy]succinimide

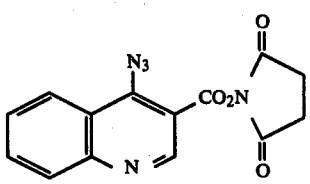

4-Azido-3-quinolinic acid monohydrate (2.3 g; 0.01 M) was suspended at ambient temperatures in dry DMF (25 ml). N-hydroxysuccinimide (1.2 g; 0.01 M) was added and the resulting mixture cooled to 0°-5° C. N,N-dicyclohexylcarbodi-imide (2.3 g; 0.11 M) was added and the mixture stirred at 0°-5° C. for ½ hr. then at ambient temperatures for 4 days. The insoluble material was removed by filtration and the filtrate evaporated to dryness in vacuo. The residual solid was recrystallized from iso-propyl alcohol as a light-brown, crystalline solid, 2.5 g. (80%), m.p. 173°-5° C. (dec.)(Found: C, 53.71; H, 2.80; N, 22.47%. C$_{14}$H$_9$N$_5$O$_4$ requires: C, 54.02; H, 2.89; N, 22.47%), $\nu_{max}$ (KBr), 2120, 1790, 1760, 1730, 1490, 1390, 1370, 1202, 890, 780, 640cm$^{-1}$, δ[(CD$_3$)$_2$SO] 2.9(s)(CH$_2$CH$_2$), 7.57-8.4(m), 9.18(s) (aromatic protons), m/e 311(M+)

(d) 6-[D-α-(4-Azidoquinoline-3-carboxamido)-phenylacetamido]penicillanic acid

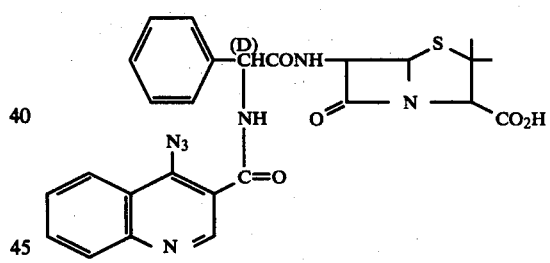

N-(4-Azido-3-quinolinoyloxy)succinimide (1.6 g; 0.005 M) was dissolved in acetone (250 ml) and added to H$_2$O (100 ml) containing sodium 6-(D-α-aminophenylacetamido)penicillanate (1.9 g; 0.005 M). The mixture was stirred at ambient temperatures for 3 hrs before the acetone was removed in vacuo. The insoluble material, 0.83 g; m.p. 166°-68° C. (dec.), was filtered, washed with H$_2$O and dried in air and shown by I.R. spectroscopy to be recovered 'activated' ester. The filtrate was acidified to pH 2.5 with 5 M HCl and the product, 0.6 g. (57%), filtered, washed with H$_2$O and dried over P$_2$O$_5$ in vacuo $\nu_{max}$ (KBr) 3100-3700(br), 2122, 1780, 1735, 1650, 1495, 1380, 1300, 1220, 770, 700cm$^{-1}$, δ[(CD$_3$)$_2$SO] 1.42(s), 1.56(s) (gem dimethyls), 4.22(s) (C$_3$ proton), 5.37-5.7(m)(β-lactams), 6.05(d)(α-proton), 7.2-8.4(m), 8.88(s) (aromatic+heteroaromatic protons), 9.2(d), 9.68(d) (2×CONH*), CO$_2$H* diffuse, low field resonance, *exchangeable with D$_2$O. biochromatogram, Rf (B/E/W) ≃ 0.80 (single zone).

(e)
6-[D-α-(4-Aminoquinoline-3-carboxamido)-phenylacetamido]penicillanic acid

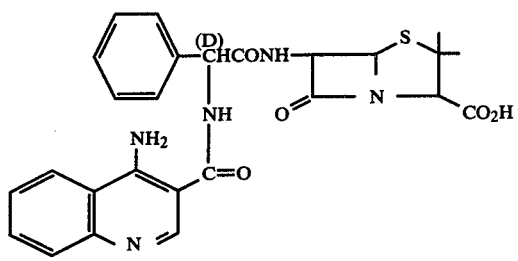

5% Pd/CaCO₃ (0.1 g) was suspended in H₂O (10 ml) and hydrogenated at ambient temperatures and atmospheric pressure for 1 hour. After 1 hour a solution in H₂O (10 ml) of 6-[D-α-(4-Aminoquinoline-3-carboxamido)phenylacetamido]penicillanic acid (0.1 g; 0.00018 M) and NaHCO₃(0.016 g; 0.00018 M) was added and the mixture hydrogenated at ambient temperatures and atmospheric pressure for 1 hour. The reaction mixture was filtered through Kieselgühr and the filtrate acidified to pH 2.5 with 5 M HCl to precipitate the product, 80 mg. (86%), $\nu_{max}$ (nujol) 3300(br), 1763, 1640, 1610, 1520(br), 1320, 770, 735, 705cm⁻¹, δ [(CD₃)₂SO] 1.39(s), 1.49(s) (gem dimethyls), 4.15(s)(C₃ proton), 5.3–5.6 (m) (β-lactams), 5.84(d) (α-proton), 7.4–7.9(m), 8.2–8.7(m), 8.72–9.1(br)(aromatics+-heteroaromatics+2 X CONH*) NH₂* and CO₂H* broad, diffuse low field resonances, *exchangeable with D₂O, biochromatogram Rf(B/E/W) ≃ 0.7 (single zone).

EXAMPLE 2

(a)
N-[7-Aminopyrazolo[1,5-a]pyrimidine-6-carbonyloxy]-succinimide

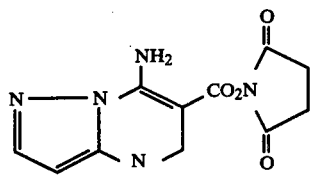

7-Aminopyrazolo[1,5-a]pyrimidine-6-carboxylic acid²(0.18 g; 0.001 M) was suspended in dry D.M.F. (15 ml) and the mixture stirred and cooled at 0°–5° C. N-hydroxysuccinimide (0.13 g; 0.0011 M) was added followed by SOCl₂ (0.15 g; ;0.0013 M), which was added dropwise. After 15 min. at 0°–5° C., SOCl₂ (0.15 g.; 0.0013 M) was again added dropwise and a clear solution was obtained. The reaction was stirred at 0°–5° C. for ½ hr. then at ambient temperatures for 24 hr. After 24 hr., the reaction mixture was cooled to 0°–5° C. and pyridine (0.42 g; 0.006 M) added dropwise. Stirred at 0°–5° C. for 1 hr., then at ambient temperatures for 4 hr. The reaction mixture was kept at 0° C. overnight and the solvent removed in vacuo. The product was precipitated from solution at low volume by addition of H₂O and collected, washed well with H₂O and dried over P₂O₅ in vacuo, 0.146 g. (53%), m.p. 294°–6° C. (dec.), $\sigma_{max}$ (nujol) 3040, 1785, 1737(br), 1680, 1615, 1580, 1455, 1445, 1350, 1290, 1198, 1060cm⁻¹, δ [(CD₃)₂SO] 2.8(s)(CH₂CH₂), 6.33(d) 7.9(d), 8.73(s) (heteroaromatic protons), NH₂* broad, diffuse low-field resonance, *exchangeable with D₂O, m/e 275(M⁺).

(b)
6-[D-α-(7-Aminopyrazolo[1,5-a]pyrimidine-6-carboxamido)phenylacetamido]penicillanic acid

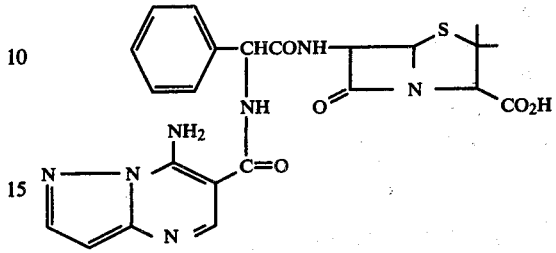

N-[7-Aminopyrazole[1,5-a]pyrimidine-6-carbonyloxy]succinimide (0.213 g; 0.0008 M) was suspended in dry D.M.F. (6 ml) at ambient temperatures and with vigorous stirring. Sodium 6-(D-α-aminophenylacetamido)-penicillanate (0.28 g; 0.0008 M) dissolved in dry D.M.F. (2 ml) was added and the mixture stirred at ambient temperatures for 1½ hr. The reaction mixture was added slowly to a large volume of rapidly-stirred, dry Et₂O and the resulting precipitate was filtered off, washed well with dry Et₂O and redissolved in H₂O (min. volume). The aqueous solution was filtered and the filtrate acidified to ph 2.5 with 5 M HCl and the resulting precipitate, 0.104 g. (25%), collected, washed well with H₂O and dried over P₂O₅ in vacuo., $\nu_{max}$ (KBr) 3600–3100(br), 3040, 1770, 1725, 1670(br), 1620, 1582, 1520(br), 1460, 1300, 1210, 789, 700 cm⁻¹, δ [(CD₃)₂SO] 1.45(s), 1.59(s) (gem dimethyls), 4.25(s) (C₃ proton), 5.35–5.73(m) (β-lactams), 6.0(d) (α-proton), 6.4(d), 8.05(d), 8.67(s) (heterocyclic protons), 7.4(br) (aromatic protons), 9.3(d), 9.9(d) (2 x CONH*), NH₂* diffuse between 5.3 and 6.9, CO₂H* diffuse, low-field resonance, *exchangeable with D₂O, biochromatogram, Rf (B/E/W) ≃0.3 (single zone), hydroxylamine assay 75% (v.Pen G.)

EXAMPLE 3

6-[D-α-(2-Aminopyridine-3-carboxamido)-phenylacetamido]penicillanic acid

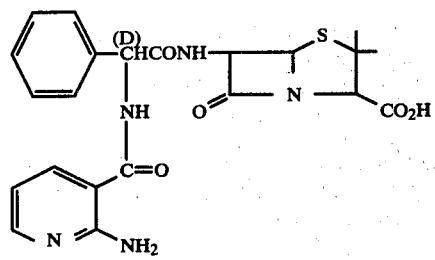

Sodium 6-(D-α-aminophenylacetamido)penicillanate (1.8 g; 0.0048 M) was dissolved in H₂O (20 ml.) at ambient temperatures with stirring and 2,4-dihydro-2,4-dioxo-1-H-pyrido[2,3-d][1,3]oxazine³ added. The mixture was stirred at ambient temperatures for 1 hr. and the insoluble material removed by filtration, m.p. 212°–213° C. (dec.). This was shown by i.r. spectroscopy to be recovered 2,4-dihydro-2,4-dioxo-1-H-pyrido[2,3-d][1,3]oxazine.

The filtrate was cooled to 0°–5° C. and acidified to pH 2.6 with 5 M HCl and the precipitate collected by filtration, washed well with H₂O and dried over P₂O₅ in vacuo, 0.4 g. (18%), $\nu_{max}$ (KBr) 3700–3100(br), 1770, 1700–1600(br), 1570, 1500, 1315, 1250, 770, 700 cm⁻¹, δ[(CD₃)₂SO] 1.41(s), 1.52(s), (gem dimethyls), 4.22(s) (C₃ proton), 5.3–5.7(m) (β-lactams), 5.87(d) (α-proton), 6.45–6.79(m), 7.2–7.7(br), 7.95–8.2(m) (aromatic+-heteroaromatic protons), 6.79–7.2(br) (NH₂*), 8.8(d), 9.03(d) (2 x CONH*), CO₂H* diffuse, low-field resonance, biochromatogram, Rf (B/E/W) ≃ 0.53 (single zone), hydroxylamine assay 93% (v. Pen.G).

EXAMPLE 4

(a)

6-[D-α-(4-Azidoquinoline-3-carboxamido)-α-(4-hydroxyphenyl)acetamido]penicillanic acid

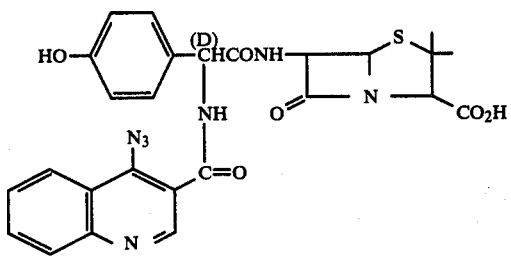

N-(4-Azido-3-quinolinoyloxy)succinimide (0.7 g; 0.0022 M) was dissolved with stirring at 0°–5° C. in the min., dry D.M.F. (20 ml). Triethylammonium 6-(D-α-amino-α-(4-hydroxyphenyl)acetamido)penicillanate (1.05 g.; 0.0022 M) was added and the mixture stirred at 0°–5° C. for 1 hr. then allowed to regain ambient temperatures over ½ hr. The reaction mixture was poured carefully into rapidly-stirred, dry Et₂O (2½ l) and the precipitate removed by filtration, carefully washed with dry Et₂O and immediately redissolved in H₂O (50 ml). The aqueous mixture was filtered and the pH adjusted to 2.5 with 5 M HCl. The product was filtered off, washed well with H₂O and dried over P₂O₅ in vacuo (0.8 g; 65%), $\nu_{max}$ (KBr) 3700–3100 (br), 2138, 1775, 1740, 1645 (br), 1618, 1519, 1380, 1227, 770 cm⁻¹., δ [(CD₃)₂SO] 1.4(s), 1.52(s) (gem dimethyls), 4.27(s) (C₃ proton), 5.4–5.8 (m) (β-lactams), 5.94(d) (α-proton), 6.79(d), 7.4 (d) (p-HO—C₆H₄—), 7.6–8.4 (m), 8.9 (s) (heterocyclic protons), 9.06 (d), 9.59 (d) (2 x CONH*), OH* and CO₂H* diffuse, low-field resonances, *exchangeable with D₂O, biochromatogram, Rf (B/E/W) ≃ 0.68, hydroxylamine assay 97.7% (versus Pen.G)

(b)

6-[D-α-(4-Aminoquinoline-3-carboxamido)-α-(4-hydroxyphenyl)acetamido]penicillanic acid (AB 20196)

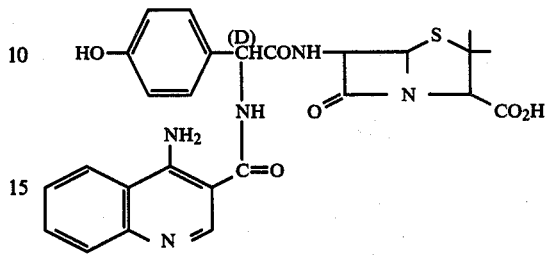

6-[D-α-(4-Azido-3-quinolinamido)-α-(4-hydroxyphenyl)acetamido]penicillanic acid (0.4 g; 0.0007 M) was suspended in H₂O (25 ml) and the mixture stirred at ambient temperatures. NaHCO₃ (0.06 g; 0.007 M) was added and the mixture stirred until complete solution had been obtained. This solution was added to a suspension of 5% Pd/CaCO₃ in H₂O (10 ml) which had been prehydrogenated for 1 hr. at atmospheric pressure and ambient temperatures. This mixture was then hydrogenated for 1¼ hr. at atmospheric pressure and ambient temperatures before the catalyst was removed by filtration through Kieselgühr and the filtrate acidified to pH 2.8 with 5 M HCl and the product (0.3; 75%) collected by filtration, washed with cold H₂O and dried over P₂O₅ in vacuo, $\nu_{max}$ (KBr) 3700–2300 (br), 1768, 1640 (br), 1610, 1510, 1380, 1320, 1250, 770 cm⁻¹, δ [(CD₃)₂SO] 1.40(s), 1.50(s) (gem dimethyls), 4.17(s) (C₃ proton), 4.5–5.9 (br) (3 x H₂O*), 5.3–5.7(m) (β-lactams), 5.73 (d) (α-proton), 6.72 (d), 7.31(d) (p-HO—C₆H₄—), 7.4–9.1 (m) (heterocyclic protons+2 x CONH*+NH₃⁺*), OH* diffuse, low-field resonance, *exchangeable with D₂O, biochromatogram, Rf (B/E/W) ≃ 0.58, hydroxylamine assay 102.0% (versus Pen. G.).

EXAMPLE 5

(a)

2-(2,2-Dicarbethoxy-1-vinylamino)-6-methylpyridine

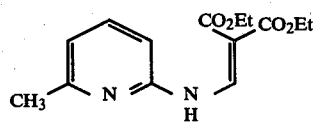

2-Amino-6-methylpyridine (108 g; 1 M) and diethyl ethoxymethylenemalonate (216 g; 1 M) were mixed together and refluxed for 2 hr. in EtOH (250 ml). The reaction mixture was left at ambient temperatures overnight and the product was filtered off, washed with EtOH and dried in vacuo over P₂O₅ (249.7 g; 90%), m.p. 107°–8° C.

(b) 3-Carbethoxy-4-hydroxy-7-methyl-1,8-naphthyridine

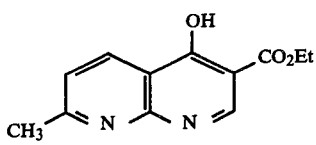

2-(2,2-Dicarbethoxy-1-vinylamino)-6-methylpyridine (47.2 g; 0.17 M) was added to vigorously refluxing diphenyl ether (300 ml) and the mixture refluxed 20 min. The reaction mixture was allowed to regain ambient temperatures and the product removed by filtration, washed well with petroleum ether (40°-60°), dissolved in boiling MeOH and the solution was decolourised by refluxing with for ½ hr. The charcoal was removed by filtration through Kieselgühr and the MeOH removed in vacuo to dryness. The residual yellow solid was stirred in CHCl₃ and the product filtered off, washed with CHCl₃ and dried in air, 10.5 g. (26%), m.p. 270°-271° C. (dec.).

(c) 3-Carbethoxy-4-chloro-7-methyl-1,8-naphthyridine

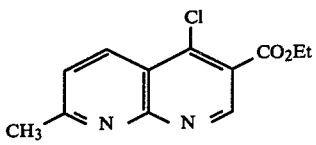

3-Carbethoxy-4-hydroxy-7-methyl-1,8-naphthyridine (3.8 g; 0.016 M) was suspended in POCl₃ (46 ml; 0.45 M) and the mixture heated at 70°-80° C. for 4 hr. The solution was concentrated in vacuo and the residue poured carefully onto crushed ice. The resulting solution was basified with 10% aq. NaOH to pH 6 and extracted with Et₂O. The Et₂O extracts were combined, washed with saturated brine and dried over anhydrous MgSO₄. The drying agent was removed by filtration and the filtrate was decolourised by refluxing with charcoal, filtered through Kieselgühr and evaporated to dryness in vacuo to yield the product, 3.7 g. (92%), m.p. 92°-93° C. (dec.). An analytical sample was obtained by chromatography over silica gel using CHCl₃/MeOH (9:1) as eluent. m.p. 90°-91° C. (dec.) (Found: N, 11.36; C, 57.80; H, 4.66; Cl, 14.13%. $C_{12}H_{11}ClN_2O_2$ requires: N, 11.18; C, 57.48; H, 4.39; Cl, 14.17%), $\nu_{max}$ (KBr) 1720, 1600, 1580, 1470, 1260, 1213, 1170, 1022, 810 cm⁻¹, δ [(CD₃)₂SO] 1.39 (t), 4.4 (q), (CH₃CH₂), 2.74 (s) (CH₃), 7.69 (d), 8.6 (d), 9.21 (s) (heterocyclic protons), m/e 250 (M+; 100%), 222 (41%).

(d) 4-Azido-3-carbethoxy-7-methyl-1,8-naphthyridine

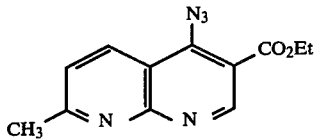

3-Carbethoxy-4-chloro-7-methyl-1,8-naphthyridine (0.8 g; 0.03 M) was dissolved in dry D.M.F. (5 ml) at ambient temperatures and NaN₃ (0.5 g; 0.007 M) added. This mixture was stirred for 20 hr. at ambient temperatures and then poured into a large volume (1 l) of H₂O. The product (0.64 g; 83%), m.p. 114°-115° C. (dec.), was filtered off, washed with H₂O and dried over P₂O₅ in vacuo (Found: N, 27.49; C, 55.59; H, 4.50%. $C_{12}H_{11}N_5O_2$ requires: N, 27.24; C, 56.03; H, 4.28%), $\nu_{max}$ (KBr) 3080, 2900, 2142, 1708, 1600, 1550, 1472, 1375, 1268, 1210, 1194, 1050, 1038, 806 cm⁻¹, δ [(CD₃)₂SO] 1.38 (t), 4.40 (q), (CH₃CH₂), 2.68 (s), (CH₃), 7.5 (d), 8.5 (d), 9.14 (s) (heterocyclic protons), m/e 257 (M+; 65%) 229 (M+—N₂; 32%), 212 (M+—OC₂H₅; 15%), 201 (52%), 133 (100%).

(e) 4-Azido-7-methyl-1,8-naphthyridine-3-carboxylic acid

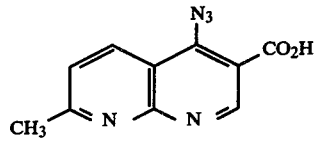

4-Azido-3-carbethoxy-7-methyl-1,8-naphthyridine (2.4 g; 0.008 M) was suspended in 10% aq. NaOH (60 ml) and the mixture stirred at ambient temperatures until all the ester had reacted. The insoluble material was removed by filtration and redissolved in H₂O. The pH of the solution was adjusted to 3.5 with 5 M HCl and the resulting precipitate (1.3 g; 71%) filtered off, washed with H₂O and dried over P₂O₅ in vacuo, m.p. 198° C. (explosive dec. on rapid heating), (Found: N, 29.66%; $C_{10}H_7N_5O_2.\frac{1}{2}H_2O$ requires N, 29.41%), m/e 201 (M+—N₂; 95%), 159 (100%) $\nu_{max}$ (KBr) 3430 (br), 2430 (br), 2150, 2060-1800 (br), 1705, 1605, 1560, 1475, 1375, 1260, 1230, 1202, 920, 810 cm⁻¹, δ [(CD₃)₂SO] 2.72 (s) (CH₃), 7.62 (d), 8.62 (d), 9.29 (s) (heterocyclic protons), CO₂H* diffuse low-field resonance, *exchangeable with D₂O.

(f) 6-(D-α-(4-Azido-7-methyl-1,8-naphthyridine-3-carboxamido)phenylacetamido]pencillanic acid

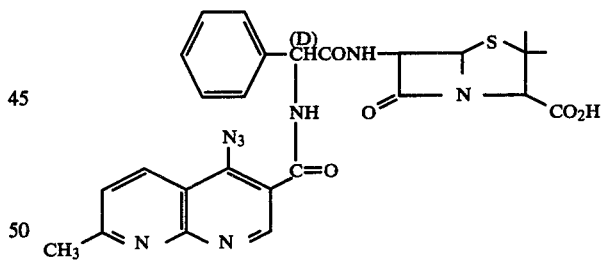

4-Azido-7-methyl-1,8-naphthyridine-3-carboxylic acid hemihydrate (1.19 g; 0.005 M) was suspended in dry D.M.F. (50 ml) at 0°-5° C. and the mixture rapidly stirred. N-hydroxysuccinimide (0.6 g; 0.005 M) and N,N'-dicyclohexylcarbodiimide (1.13 g; 0.0055 M) were added and the reaction mixture stirred at 0°-5° C. for 1 hr. then at ambient temperatures for 4 days. The reaction mixture was cooled to 0°-5° C. again and sodium 6-(D-α-aminophenylacetamido)penicillanate (1.8 g; 0.005 M) added. This mixture was stirred at 0°-5° C. for 1 hr. and allowed to regain ambient temperatures over ½ hr. The mixture was filtered into rapidly-stirred, dry Et₂O (2 l) and the resulting precipitate filtered off, washed well with dry Et₂O and immediately redissolved in H₂O (50 ml). The aqueous mixture was filtered and the pH adjusted to 2.5 with 5 M HCl. The product (0.8 g; 32%) was collected by filtration, washed with H₂O and dried over P₂O₅ in vacuo, $v_{max}$ (KBr) 3700–3100 (br), 2140, 1775, 1738, 1650 (br), 1602, 1520 (br), 1380, 1350–1250 (br), 1225, 808, 702 cm⁻¹., δ [(CD₃)₂SO] 1.43 (s), 1.57 (s) (gem dimethyls), 2.71 (s) (CH₃), 4.23 (s) (C₃ proton) 5.3–5.7 (m) (β-lactams), 6.03 (s) (α-proton), 7.2–7.8 (m), 8.55 (d), 9.01 (s) (aromatic+-heteroaromatic protons), 9.2 (d), 9.7 (d) (2×CONH*), CO₂H* diffuse, low-field resonance, *exchangeable with D₂O, biochromatogram, Rf (B/E/W). ≃0.43, hydroxylamine assay 98.7% (versus Pen G.).

(g)
6-[D-α-(4-Amino-7-methyl-1,8-naphthyridine-3-carboxamido)phenylacetamido]penicillanic acid

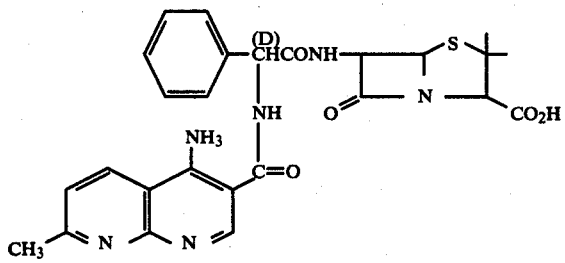

6-[D-α-(4-Azido-7-methyl-1,8-naphthyridine-3-carboxamido)phenylacetamido]penicillanic acid (0.56 g; 0.001 M) was dissolved in H₂O (20 ml) containing NaHCO₃ (0.084 g; 0.001 M). This solution was added to a suspension of 5% Pd/CaCO₃ (0.56 g) in H₂O (10 ml), which had been pre-hydrogenated for 1 hr. at ambient temperatures and atmospheric pressure. This mixture was hydrogenated at atmospheric pressure and ambient temperatures for 1¼ hr., the catalyst removed by filtration through Kieselgühr and the filtrate acidified to pH 4 with 5 M HCl. The product (0.26 g; 49%) was collected by filtration, washed with H₂O and dried over P₂O₅ in vacuo, $v_{max}$ (KBr) 3700–2200 (br), 1765, 1700–1550 (br), 1515, 1460, 1370, 1325, 1260, 1220, 1080, 800, 702 cm⁻¹, δ [(CD₃)₂SO] 1.41 (s), 1.51 (s) (gem dimethyls), 2.61 (s) (CH₃) 4.18 (s) (C₃ proton), 5.2–5.6 (m) (β-lactams), 5.9 (d) (α proton), 5.6–6.7 (br), (3×H₂O*), 7.0–7.8 (m), 8.1–9.3 (broad m) (aromatics+-heteroaromatics+NH₃⁺*+2×CONH*), *exchangeable with D₂O, biochromatogram, Rf (B/E/W)≃0.53, hydroxylamine assay 87% (versus Pen G.).

EXAMPLE 6

(a)
6-[D-α-(4-Azido-7-methyl-1,8-naphthyridine-3-carboxamido)-α-(4-hydroxyphenyl)acetamido]penicillanic acid

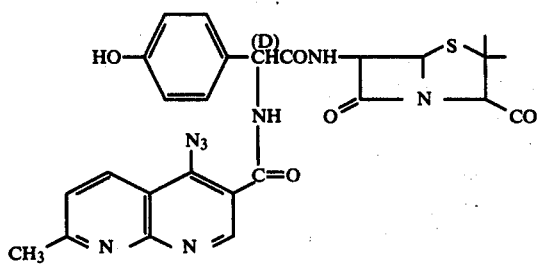

4-Azido-7-methyl-1,8-naphthyridine-3-carboxylic acid (1.15 g; 0.005 M) was suspended in dry D.M.F. (50 ml) at 0°–5° C. with stirring and N-hydroxysuccinimide (0.6 g; 0.005 M) and N,N′-dicyclohexylcarbodiimide (1.13 g; 0.0055 M) were added. The mixture was stirred at 0°–5° C. for 1 hr. and allowed to regain ambient temperatures before being stirred at ambient temperatures for 4 days. The reaction mixture was re-cooled to 0°–5° C. and triethylammonium 6-[D-α-amino-α-(4-hydroxyphenyl)acetamido]penicillanate (2.3 g; 0.0049 M) added. The reaction mixture was then stirred at 0°–5° C. for 1 hr and then allowed to regain ambient temperatures over ½ hr. before being filtered into rapidly-stirred, dry Et₂O (2 l). The precipitate was filtered off, washed with dry Et₂O and immediately redissolved in H₂O (50 ml), the aqueous mixture filtered and the pH of the filtrate adjusted to 3 with 5 M HCl and the product (0.86 g; 30%) collected by filtration, washed with H₂O and dried over P₂O₅ in vacuo, $v_{max}$ (KBr) 3700–3100 (br), 2140, 1770, 1733, 1650 (br), 1601, 1510, 1380, 1270, 1230 (br), 840, 808 cm⁻¹, δ [(CD₃)₂SO] 1.46 (s), 1.60 (s) (gem dimethyls), 2.73 (s) (CH₃), 4.22 (s) (C₃ proton), 5.38–5.75 (m) (β-lactams), 5.9 (d) (α-proton), 6.79 (d), 7.4 (d) (p-HO—C₆H₄—), 7.6 (d), 8.54 (d), 9.0 (s) (heteroaromatic protons), 9.06 (d), 9.59 (d) (b 2×CONH*), CO₂H* and OH* diffuse, low-field resonances, *exchangeable with D₂O, biochromatogram, Rf (B/E/W)≃0.54, hydroxylamine assay 84.5% (versus Pen G.).

(b)
6-[D-α-(4-Amino-7-methyl-1,8-naphthyridine-3-carboxamido)-α-(4-hydroxyphenyl)acetamido]penicillanic acid

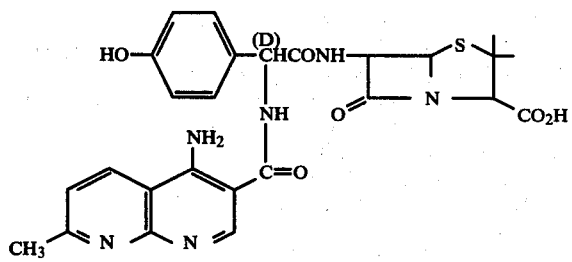

6-[D-α-(4-Azido-7-methyl-1,8-naphthyridine-3-carboxamido)-α-(4-hydroxyphenyl)acetamido]penicillanic acid (0.8 g; 0.0014 M) was dissolved in H₂O (25 ml) containing NaHCO₃ (0.12 g; 0.0014 M) and the solution added to a suspension of 5% Pd/CaCO₃ (0.8 g) in H₂O (10 ml), which had been pre-hydrogenated for 1 hr. at ambient temperatures and atmospheric pressure. The resulting mixture was hydrogenated 1¼ hr. at ambient temperatures and atmospheric pressure before the catalyst was removed by filtration through Kieselgühr. The pH of the filtrate was adjusted to 3.5 with 5 M HCl and the product (0.4 g; 47%) removed by filtration, washed with H₂O and dried over P₂O₅ in vacuo, $v_{max}$ (KBr) 3700–2250 (br), 1765, 1700–1550 (br), 1510, 1460, 1370, 1325, 1265, 1245, 800 cm⁻¹, δ [(CD₃)₂SO] 1.41 (s), 1.50 (s) (gem dimethyls), 2.60 (s) (CH₃), 4.15 (s) (C₃ proton), 5.3–5.6 (m) (β-lactams), 5.7 (d) (α-proton), 5.8–6.5 (br), (3×H₂O*), 6.7 (d) 6.28 (d) (p-HO—C₆H₄—), 7.37 (d) 8.1–9.3 (m, broad) (heteroaromatic protons+NH₃⁺*+2×CONH*), *exchangeable with D₂O, biochromatogram, Rf (B/E/W)≃0.36, hydroxylamine assay 96.6% (versus Pen.G).

EXAMPLE 7

(a) Ethyl-4-azido-7-chloroquinoline-3-carboxylate

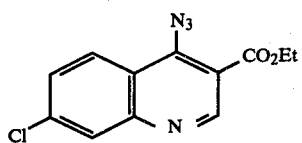

Sodium azide (0.62 g; 0.009 M) was suspended in a solution of ethyl-4,7-dichloroquinoline-3-carboxylate E. F. Elslager, et al., J. Med. Pharm, Chem, 5, 550 (1962) (1.75 g; 0.006 M) in dry dimethyl formamide (20 ml) and this mixture stirred at ambient temperatures. After 18 hr. the mixture was poured into reapidly stirred water (200 ml), the resultant precipitate filtered off, dried at the pump and then recrystallised from ethanol (8 ml/g), 1.27 g (71%), m.p. 94.5° C., (Found: C, 51.7; H, 3.4; N, 20.2; Cl, 12.9% $C_{12}H_9N_4O_2Cl$ requires C, 52.0; H, 3.3; N, 20.2; Cl, 12.8%); max (KBr) 2140, 1722, 1390, 1372, 1274, 1239, 1199 and 1058 cm$^{-1}$, (CDCl$_3$) 1.48 (t) and 4.55 (m) (CH$_3$CH$_2$), 7.59 (m), 8.11 (d), 8.32 (d) and 9.29 (s) (aromatic H's) m/e 276 (M+, 14%), 248 (9%), 218 (22%), 154 (29% 152 (100%).

(b) 4-Azido-7-chloroquinoline-3-carboxylic acid

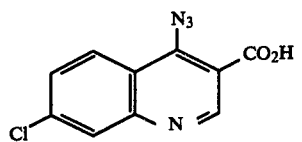

Ethyl-4-azido-7-chloroquinoline-3-carboxylate (0.57 g; 0.002 M) in 10% aq. NaOH (10 ml) and stirred at 40° C. for 5 hr. The unreacted ester, m.p. 91°-4° C., was filtered off, the filtrate acidified to pH 3 with 5 M HCl, the product filtered off, washed well with water and dried in vacuo over P$_2$O$_5$, 0.33 g (66%), m.p. 284°-6° C. (dec.), (Found: C, 46.7; H, 2.3; Cl 14.1%. $C_{10}H_5ClN_4O_2.\frac{1}{2}H_2O$ requires C, 46.6; H, 2.4; Cl 13.8%), $v_{max}$ (KBr) 2158, 1705 (br), 1608, 1562, 1395 (br), 1210 and 798 cm$^{-1}$, δ [(CD$_3$)$_2$SO] 7.72 (m), 8.09 (d), 8.36 (d) and 9.18 (s) (aromatic H's)

(c)
6-[D-α-(4-Azido-7-chloroquinoline-3-carboxamido)-phenylacetamido]penicillanic acid

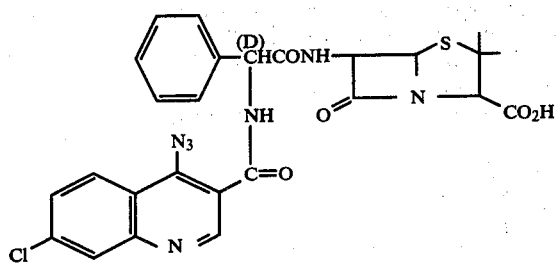

4-Azido-7-chloroquinoline-3-carboxylic acid (0.7 g; 0.0028 M) was dissolved at 0°-5° C. in dry D.M.F. (25 ml) and to the stirred solution was added N-hydroxysuccinimide (0.33 g; 0.0028 M) and N,N'-dicyclohexycarbodiimide (0.63 g; 0.03 M). After stirring for 1 hr. at 0°-5° C. the reaction was allowed to regain ambient temperatures and stirred at ambient temperatures overnight. Sodium ampicillin (1.0 g; 0.0028 M) was added to the reaction at 0°-5° C. and the reaction mixture stirred at 0°-5° C. for 1 hr. and allowed to reach ambient temperatures over ½ hr. The reaction mixture was then poured into rapidly-stirred, dry Et$_2$O (2 l) and the precipitate removed by filtration, washed with dry Et$_2$O and immediately redissolved in H$_2$O (50 ml). The aqueous mixture was filtered and the pH of the filtrate adjusted to 2.5 with 5 M HCl in the presence of EtOAc (50 ml). The layers were separated, the aqueous phase extracted with EtOAc (2×50 ml), the extracts combined, washed with H$_2$O at pH 2 (2×25 ml), saturated brine (25 ml) and dried over anhydrous MgSO$_4$. The solvent was concentrated in vacuo, diluted with dry Et$_2$O and the product collected by filtration, washed with dry Et$_2$O and dried over P$_2$O$_5$ in vacuo, 0.22 g (14%), $v_{max}$ (KBr) 3700-3100 (br), 2238, 1775, 1730, 1650, 1608, 1520, 1379, 1300, 1212, 702 cm$^{-1}$, δ [(CD$_3$)$_2$SO] 1.4 (s), 1.53 (s) (gem dimethyls), 4.19 (s) (C$_3$ proton), 5.3-5.6 (m) (β-lactams), 5.99 (d) (α-proton), 7.1-7.8 (m), 8.02 (d), 8.16 (d), 8.81 (s) (aromatic+heteroaromatic protons), 9.12 (d), 9.60 (d) (2×CONH*), CO$_2$H* diffuse, low-field resonance, biochromatogram, Rf (B/E/W) = 0.74, hydroxylamine assay 82.1% (versus Pen G.).

(d)
6-[D-α-(4-Amino-7-chloroquinoline-3-carboxamido)-phenylacetamido]penicillanic acid

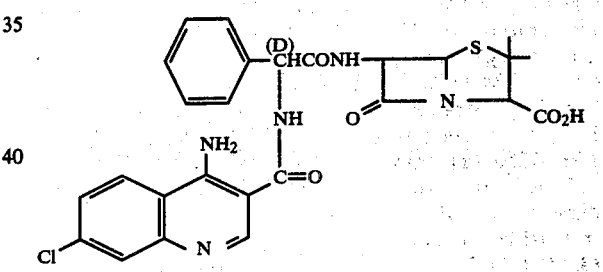

6-[D-α-(4-Azido-7-chloroquinoline-3-carboxamido)-phenylacetamido]penicillanic acid (0.64 g; 0.0011 M) was dissolved in H$_2$O (20 ml) containing NaHCO$_3$ (0.09 g; 0.0011 M). This solution was added to a suspension in H$_2$O (10 ml) of 5% Pd/CaCO$_3$ (0.64 g), which had been pre-hydrogenated for 1 hr. at ambient temperatures and atmospheric pressure. The mixture was hydrogenated for 1¼ hr. at ambient temperatures and atmospheric pressure before the catalyst was removed by filtration through Kieselgühr and the filtrate acidified to pH 3 with 5 M HCl. The product (0.2 g; 30%) was collected by filtration, washed with H$_2$O and dried over P$_2$O$_5$ in vacuo, $v_{max}$ (KBr) 3700-2250 (br), 1765, 1700-1570, 1550, 1515, 1371, 1325, 1250, 1212, 790, 701 cm$^{-1}$, δ [(CD$_3$)$_2$SO] 1.42 (s), 1.51 (s) (gem dimethyls), 4.19 (s) (C$_3$ proton), 5.2-6.2 (broad m) (3×H$_2$O*+β-lactams-+α-proton), 7.0-7.7 (broad m), 7.8 (broad), 8.2-8.5 (broad), 7.6-9.3 (broad) (aromatic+heteroaromatics protons+NH$_3$+*+2×CONH*), *exchangeable with D$_2$O, biochromatogram, Rf (B/E/W)=0.74.

EXAMPLE 8

(a) 6-[D-α-(4-Azido-7-chloroquinoline-3-carboxamido)-α-(4-hydroxyphenyl)acetamido]penicillanic acid

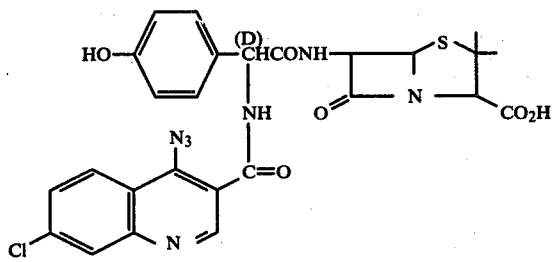

4-Azido-7-chloroquinoline-3-carboxylic acid (0.57 g; 0.0023 M) was dissolved at 0°–5° C. in dry D.M.F. (15 ml). To this stirred, cold solution was added N-hydroxysuccinimide (0.26 g; 0.0023 M) and N,N'-dicyclohexylcarbodiimide (0.52 g; 0.0025 M) and the mixture stirred at 0°–5° C. for 1 hr. and allowed to regain ambient temperatures. The reaction was stirred at ambient temperatures overnight and then cooled to 0°–5° C. Triethylammonium 6-[D-α-amino-α-(4-hydroxyphenyl)acetamido]penicillanate (1.0 g; 0.0021 M) was added and the mixture stirred at 0°–5° C. for 1 hr. and allowed to regain ambient temperatures over ½ hr. The reaction mixture was filtered into rapidly-stirred, dry $Et_2O$ (2 l) and the precipitate removed by filtration, washed with dry $Et_2O$ and immediately added to $H_2O$ (50 ml). The mixture was filtered and the pH of the filtrate adjusted to 2.8 with 5 M HCl. The product (0.52 g; 38%) was collected by filtration, washed with $H_2O$ and dried over $P_2O_5$ in vacuo, $\nu_{max}$ (KBr) 3700–3100 (br), 2140, 1770, 1740, 1645, 1610, 1515, 1380, 1240, 840 cm$^{-1}$, δ [$(CD_3)_2SO$] 1.4 (s), 1.55 (s) (gem dimethyls), 4.16 (s) ($C_3$ proton), 5.3–5.64 (m) (β-lactams), 5.82 (d) (α-proton), 6.68 (d), 7.28 (d) (p-HO—$C_6\underline{H}_4$—), 7.62 (dd), 9.03 (d), 8.17 (d), 8.8 (s) (heteroaromatic protons), 8.99 (d), 9.5 (d) (2×CONH*), OH* and $CO_2H$* diffuse, low-field resonances, biochromatogram, Rf (B/E/W) ≃ 0.70, hydroxylamine assay 82.1% (versus Pen G.).

(b) 6-[D-α-(4-Amino-7-chloroquinoline-3-carboxamido)-α-(4-hydroxyphenyl) acetamido]penicillanic acid (9)

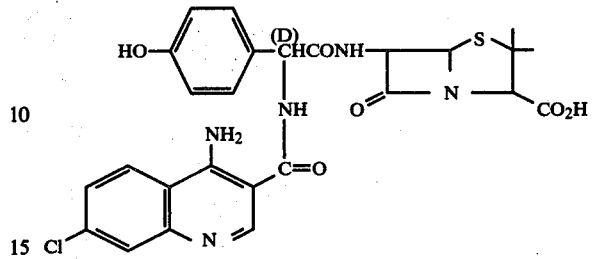

6-[D-α-(4-Azido-7-chloroquinoline-3-carboxamido)-α-(4-hydroxyphenyl) acetamido]penicillanic acid (0.5 g; 0.00084 M) was dissolved in $H_2O$ (20 ml) containing $NaHCO_3$ (0.07 g; 0.00083 M). This solution was added to a suspension of 5% Pd/$CaCO_3$ (0.5 g) in $H_2O$ (10 ml) which had been pre-hydrogenated for 1 hr. at atmospheric pressure and ambient temperatures. The reaction mixture was hydrogenated at atmospheric pressure and ambient temperatures for 1¼ hr. before the catalyst was removed by filtration through Kieselgühr. The pH of the filtrate was adjusted to 3 and the product removed by filtration, 0.32 g. (61%), washed with $H_2O$ and dried over $P_2O_5$ in vacuo, $\nu_{max}$ (KBr) 3700–2250 (br), 1760, 1700–1560 (2 broad peaks), 1510, 1470, 1370, 1320, 1250, 1180, 913, 890, 790 cm$^{-1}$, δ[$(CD_3)_2SO$] 1.4 (s), 1.5 (s) (gem dimethyl), 4.16 (s) ($C_3$ proton), 5.0–6.5 (broad) (3×$H_2O$*), 5.35–5.60 (m) (β-lactams), 5.7 (d) (α-proton), 6.68 (d), 7.27 (d) (pHO—$C_6\underline{H}_4$—), 7.34 (dd), 7.8 (d), 8.2–8.58 (br), 8.62–9.1 (br) (heteroaromatic protons+2×CONH*+$NH_3^+$*),* exchangeable with $D_2O$, biochromatogram, Rf (B/E/W) ≃ 0.63, hydroxylamine assay 96.2% (versus Pen.G.),

BIOLOGICAL DATA

Table 1 and 2 show the antibacterial activity of the compounds of Examples 1–8, in terms of their minimum inhibitory concentrations (in mg/ml) against a range of organisms determed in nutrient agor. The figures in brackets represent values determined in broth.

Table 3 shows the activity of some of the compounds of the invention against a number of strains of *Pseudomonas aeruginosa*. For comporsion purposes. The activity of ticarcillin in the same test is shown.

TABLE 1

In Vitro Primary Antibacterial Evaluation

| Reference No: | AB 20176 | AB 20196 | AB 20214 | AB 20215 | AB 20221 | AB 20213 |
|---|---|---|---|---|---|---|
| X—⌬—CHCO.APA, NH, CO, R | R | (NH₂ quinoline) | (NH₂ quinoline) | (NH₂ naphthyridine-CH₃) | (NH₂ naphthyridine-CH₃) | (NH₂ quinoline-Cl) | (NH₂ quinoline-Cl) |
| X | | H | HO | H | HO | H | HO |
| Compound of Example No: | | 1 | 4 | 5 | 6 | 7 | 8 |
| Purity (%) | | ~90% | ~95% | ~80% | ~90% | ~70% | ~90% |
| MINIMUM INHIBITORY CONCENTRATIONS (µg/ml) | | | | | | | |
| *E. coli* JT 1 | | 5.0 (2.5) | 25 (2.5) | 12.5 (12.5) | 5.0 (2.5) | 5.0 | 12.5 (12.5) |
| *E. coli* JT 4 | | >100 | >500 | >500 | >500 | >500 | >500 |
| *E. coli* JT 425 | | 25 | 25 | 50 | 50 | 12.5 | 25 |
| *E. coli* NCTC 10418 | | 2.5 (1.0) | 25 (2.5) | 5.0 (2.5) | 5.0 (2.5) | 12.5 | 12.5 (2.5) |
| *Ps. aeruginosa* 10662 nt. | | 10 (10) | 25 (2.5) | 12.5 (12.5) | 5.0 | 50 | 125 (12.5) |
| *Ps. aeruginosa* 10662 10$^{-2}$ | | 2.5 (2.5) | 12.5 (2.5) | 0.5 (5.0) | 2.5 | 5.0 | 5.0 (1.2) |
| *Ps. aeruginosa* Dalgleish 10$^{-2}$ | | 25 | 25 | 50 | 50 | 25 | 25 |

TABLE 1-continued

In Vitro Primary Antibacterial Evaluation

| Reference No: | AB 20176 | AB 20196 | AB 20214 | AB 20215 | AB 20221 | AB 20213 |
|---|---|---|---|---|---|---|
| X—⟨⟩—CHCO.APA / NH / CO / R    R= | 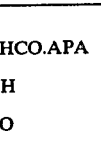 | 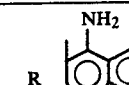 | 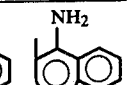 | 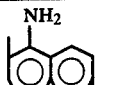 | 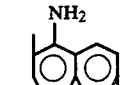 | 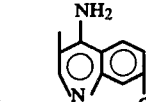 |
| X | H | HO | H | HO | H | HO |
| Compound of Example No: | 1 | 4 | 5 | 6 | 7 | 8 |
| Purity (%) | ~90% | ~95% | ~80% | ~90% | ~70% | ~90% |

MINIMUM INHIBITORY CONCENTRATIONS (μg/ml)

| | | | | | | |
|---|---|---|---|---|---|---|
| *Serratia marcescens* US 32 | 10 | 500 | 25 | 50 | 12.5 | 25 |
| *Klebsiella aerogenes* A | 50 | 500 | 50 | 125 | 50 | 125 |
| *Enterobacter cloacae* N1 | 10 | 25 | 12.5 | 12.5 | 12.5 | 12.5 |
| *P. mirabilis* C977 | 5.0 | 50 | 5.0 | 5.0 | 5.0 | 5.0 |
| *P. mirabilis* 899 | >100 | >500 | >500 | >500 | >500 | >500 |
| *P. morgani* | 10 | 25 | 12.5 | 12.5 | 12.5 | 12.5 |
| *P. rettgeri* | 25 | 25 | 12.5 | 12.5 | 25 | 25 |
| *B. subtilis* | 2.5 | 12.5 | 0.5 | 1.2 | 1.2 | 1.2 |
| *Staph. aureus* (Oxford) | 0.2 (1.0) | 1.2 (0.2) | 2.5 (0.5) | 2.5 (0.5) | 1.2 | 1.2 (0.5) |
| *Staph. aureus* (Russell) | >100 | >500 | >500 | 500 (250) | 500 | 250 |
| *Staph. aureus* 1517 | >100 | — | >500 | 500 | 500 | 500 |
| *Strep. faecalis* τ | 1.0 | 5.0 | 1.2 | 1.2 | 1.2 | 1.2 |
| β-Haemolytic Strep CN10 | ≦0.02 | 0.5 | ≦0.02 | 0.05 | ≦0.02 | ≦0.02 |

Table 2

| Reference No: | 20176 | 20115 | 20063 |
|---|---|---|---|
| ⟨⟩—CHCOAPA / NH / C=O / R   R= | (quinoline-NH₂) | (pyrazolopyrimidine-NH₂) | (pyridine-NH₂) |
| Compound of Example number: | 1 | 2 | 3 |
| Purity (%): | 70 | 75 | 90 |
| *E. coli* JT 1 | 5.0(2.5) | 25(25) | 125(50) |
| *E. coli* JT 4 | >500 | >250 | >500 |
| *E. coli* JT 425 | 25 | 125 | 500 |
| *E. coli* NCTC 10418 | 2.5(1.2) | 25(12.5) | 125(12.5) |
| *Ps. aeruginosa* 10662 nt. | — | 50(125) | 50(125) |
| *Ps. aeruginosa* 10662 $10^{-2}$ | 2.5(2.5) | 12.5(25) | 50(50) |
| *Ps. aeruginosa* Dalgleish $10^{-2}$ | 50 | 125 | 250 |
| *Serratia marcescens* JS32 | 25 | — | 125 |
| *Klebsiella aerogenes* A | 125 | 125 | 125 |
| *Enterobacter cloacae* N1 | 5.0 | 12.5 | 125 |
| *P. mirabilis* C977 | 2.5 | 12.5 | 50 |
| *P. mirabilis* 889 | >500 | >250 | >500 |
| *P. morganii* | 12.5 | 250 | >500 |
| *P. rettgeri* | 25 | 50 | 500 |
| *B. subtilis* | 5.0 | 5.0 | 2.5 |
| *Staph. aureus* Oxford | <0.1(0.01) | 5.0 | 0.2(1.2) |
| *Staph. aureus* Russell | 250 | >250 | 250(>500) |
| *Staph. aureus* 1517 | 250 | >250 | >500 |
| *Strep Faecalis* I | 0.5 | 5.0 | 1.2 |
| β-Haemolytic Strep. CN10 | <0.1 | 0.5 | 0.01 |

TABLE 3

| Example No. | Inoculum | \multicolumn{8}{c}{MIC* (mg/ml) and No. of Strains} |

| Example No. | Inoculum | 1.2 | 2.5 | 5.0 | 12.5 | 25 | 50 | 125 | 250 | 500 |
|---|---|---|---|---|---|---|---|---|---|---|
| 8 | Undiluted | | 5 | 3 | 2 | 2 | 2 | 1 | 2 | 3 |
| 5 | | 1 | 6 | 5 | 3 | 2 | 2 | 1 | | |
| 6 | | 1 | 4 | 9 | 5 | | | 1 | | |
| 4 | | | 2 | 1 | 1 | 1 | 2 | 2 | 2 | 9 |
| Ticarcillin | | | | 4 | 4 | 3 | 6 | | 2 | 1 |
| 8 | Diluted 1/100 | 11 | 4 | 3 | 2 | | | | | |
| 5 | | 8 | 10 | 1 | 1 | | | | | |

TABLE 3-continued

| Example No. | MIC* (mg/ml) and No. of Strains | | | | | | | | |
|---|---|---|---|---|---|---|---|---|---|
| | Inoculum | 1.2 | 2.5 | 5.0 | 12.5 | 25 | 50 | 125 | 250 | 500 |
| 6 | | | 5 | 9 | 4 | 2 | | | | |
| 4 | | | 5 | 12 | 1 | 2 | | | | |
| Ticarcillin | | | | | 6 | 9 | 3 | | | |

*Serial dilution in nutrient agar. inoculum 0.001 ml. o.b.c. diluted as specified

What we claim is:

1. A penicillin of formula (I) or a pharmaceutically acceptable salt or conventional penicillin in vivo hydrolysable ester thereof:

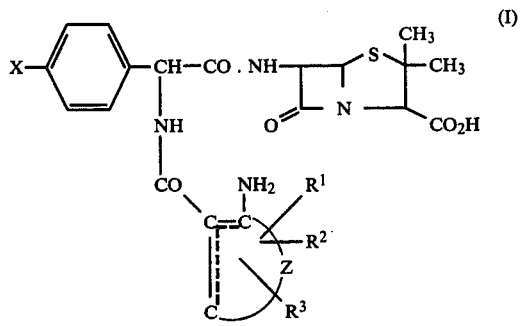

wherein
X is hydrogen or hydroxy;
the dotted line represents a double bond in one of the positions shown;
Z represents the residue of a pyridine, pyrimidine, pyridazine or 1,2,3-triazine ring;
$R^1$, $R^2$ and $R^3$ are the same or different and each represents hydrogen, halogen, $C_{1-6}$ alkyl, $C_{1-6}$ alkoxy, $C_{1-6}$ alkylthio, cyano, amino, mercapto, $C_{1-6}$ alkylamino, di-$C_{1-6}$ alkylamino, $C_{1-6}$ alkanoylamino, nitro or hydroxy or any two of $R^1$, $R^2$ and $R^3$ on adjacent carbon or nitrogen atoms represent the residue of a benzene, cyclohexane, cyclopentane, pyridine, pyrimidine, pyridazine, pyrazine, piperidine, piperazine, pyrrolidine, pyrazole, triazole, tetrazole, oxadole, triazine, thiazoline, thiazolidine or morpholine ring, and being optionally substituted with up to three substituents selected from halogen, $C_{1-6}$ alkoxy, $C_{1-6}$ alkylthio or hydroxy.

2. A penicillin as claimed in claim 1 wherein Z represents the residue of a pyridine or pyrimidine ring.

3. A penicillin as claimed in claim 1 wherein $R^3$ is hydrogen.

4. A penicillin as claimed in claim 1 wherein $R^1$ and $R^2$ together represent the residue of a benzene, cyclohexane, cyclopentane, pyridine, pyrimidine, pyridazine, pyrazine, piperidine, piperazine, pyrrolidine, pyrazole, triazole, tetrazole, oxazole, triazine, thiazoline, thiazolidine or morpholine ring.

5. A penicillin as claimed in claim 4 wherein the residue formed by $R^1$ and $R^2$ is optionally substituted with a halogen or $C_{1-6}$ alkyl group.

6. 6-[D-α-(4-Aminoquinolin-3-carboxamido)-phenylacetamido] penicillanic acid.

7. 6-[D-α-(4-Aminoquinolin-3-carboxamido)-4-hydroxyphenylacetamido] penicillanic acid.

8. 6-[D-α-(7-Aminopyrazole[1,5-a]pyrimidine-6-carboxamido] phenylacetamido penicillanic acid.

9. 6-[D-α-Aminopyrazolo[1,5-a]pyrimidine-6-carboxamido]-4-hydroxyphenylacetamido penicillanic acid.

10. 6-[D-α-(2-Aminopyridine-3-carboxamido)-phenylacetamido] penicillanic acid.

11. 6-[D-α-(2-Aminopyridine-3-carboxamido)4-hydroxyphenylacetamido]penicillanic acid.

12. 6-[D-α-(5-Amino-1,8-naphthridine-6-carboxamido)phenylacetamido] penicillanic acid.

13. 6-[D-α-(5-Amino-1,8-naphthridine-6-carboxamido)-4-hydroxyphenylacetamido]penicillanic acid.

14. 6-[D-α-(4-Amino-1,5-naphthridine-3-carboxamido)pehnylacetamido]penicillanic acid.

15. 6-[D-α-(4-Amino-1,5-naphthridine-3-carboxamido)-4-hydroxyphenylacetamido]penicillanic acid.

16. 6-[D-α-(2-Aminopyridazine-3-carboxamido)-phenylacetamido]penicillanic acid.

17. 6-[D-α-(2-Aminopyridazine-3-carboxamido)-4-hydroxyphenylacetamido]penicillanic acid.

18. 6-[D-α-(4-Amino-7-methyl-1,8-naphthridine-3-carboxamido) phenylacetamido]penicillanic acid.

19. 6-[D-α-(4-Amino-7-methyl-1,8-naphthridine-3-carboxamido)-4-hydroxyphenylacetamido]penicillanic acid.

20. 6-[D-α-(4-Amino-7-chloroquinoline-3-carboxamido) phenylacetamido]penicillanic acid.

21. 6-[D-α-(4-Amino-7-chloroquinoline-3-carboxamido)-4-hydroxyphenylacetamido]penicillanic acid.

* * * * *